United States Patent [19]

Umemura et al.

[11] Patent Number: 4,566,459

[45] Date of Patent: Jan. 28, 1986

[54] ULTRASONIC DIAGNOSIS SYSTEM

[75] Inventors: Shinichiro Umemura, Hachioji; Kageyoshi Katakura, Meguro; Toshio Ogawa, Nishitama, all of Japan

[73] Assignee: Hitachi, Ltd., Tokyo, Japan

[21] Appl. No.: 580,166

[22] Filed: Feb. 14, 1984

[30] Foreign Application Priority Data

Feb. 14, 1983 [JP] Japan ................................ 58-23548

[51] Int. Cl.⁴ .............................................. A61B 10/00
[52] U.S. Cl. ...................................... 128/660; 73/597; 73/626
[58] Field of Search ............................ 128/660–661; 73/597, 598, 602, 626

[56] References Cited

U.S. PATENT DOCUMENTS 4,105,018 8/1978 Greenleaf et al. ............... 73/597 X
4,176,658 12/1979 Kossoff et al. .................... 73/597 X

FOREIGN PATENT DOCUMENTS 3127192 1/1983 Fed. Rep. of Germany ...... 128/660
3127146 1/1983 Fed. Rep. of Germany ...... 128/660

OTHER PUBLICATIONS

Hildebrand, B. P. et al., "Mapping of Materials Stress with UTS Tomography" Paper Presented at AR-PA/AF Review of Progress, La Jolla, Cal., Jul. 1979.

*Primary Examiner*—Kyle L. Howell
*Assistant Examiner*—Francis J. Jaworski
*Attorney, Agent, or Firm*—Antonelli, Terry & Wands

[57] ABSTRACT

An ultrasonic diagnosis system comprising a variable setting arrangement including an ultrasonic transducer array for transmitting a pulse-like ultrasonic wave to an object and detecting a reflection wave from the object, and assuming the acoustic velocity of the object; a control arrangement for determining the depth of electronic focusing in accordance with this assumed acoustic velocity; and a display for displaying the assumed acoustic velocity. The ultrasonic diagnosis system determines whether the reflection signal of the object at a predetermined position is in-focus or out-of-focus and knows the actual acoustic velocity of the object from the assumed acoustic velocity when the reflection signal is in-focus.

9 Claims, 28 Drawing Figures (A) $cy > c_0y_0$ (B) $cy = c_0y_0$ (C) $cy < c_0y_0$ $$\tau(T) = \sqrt{\left(\frac{X}{C}\right)^2 + \left(\frac{T}{2}\right)^2} - \frac{T}{2}$$

ULTRASONIC DIAGNOSIS SYSTEM

BACKGROUND OF THE INVENTION

1. Field of the Invention

This invention relates generally to an ultrasonic diagnosis system and more particularly, to a ultrasonic diagnosis system which makes it possible to measure the acoustic velocity inside the body of a subject.

2. Description of the Prior Art

Studies on tissue characterization have been vigorously made in recent years in various countries and the measurement of acoustic velocity is a critical problem. The conventional methods of measuring the acoustic velocity include a singaround method and ultrasonic computer tomography. Since they are transmission methods, however, there is an inevitable limit to measuring the acoustic velocity inside the body of a subject.

On the other hand, the measuring methods of the reflection type include one that radiates ultrasonic beams from two directions to a body within a coupling tank containing an acoustic coupling liquid so as to analyze the refraction at the interface between the living body and the acoustic coupling liquid. However, this method involves the problems that incident angles at the interface should be accurately measured and that the calculation is complicated.

SUMMARY OF THE INVENTION

It is an object of the present invention to provide a method and system for measuring the acoustic velocity inside a living body by a high resolution ultrasonic diagnosis system of a reflection type.

It is another object of the present invention to provide a system which makes it possible to measure the acoustic velocity at a specific portion or a specific organ inside a living body.

In a ultrasonic diagnosis system which includes a pulse-like ultrasonic wave transmitter and a receiver and which processes an electric signal converted by a reception element forming the receiver so as to obtain an ultrasonic image of a subject, the gist of the present invention resides in that the system further includes means for varying the acoustic velocity which is to be assumed in the image formation, and means for displaying the acoustic velocity.

DESCRIPTION OF THE PREFERRED EMBODIMENTS

Hereinafter, the principle and embodiments of the present invention will be described in detail with reference to the accompanying drawings.

Figure 1:
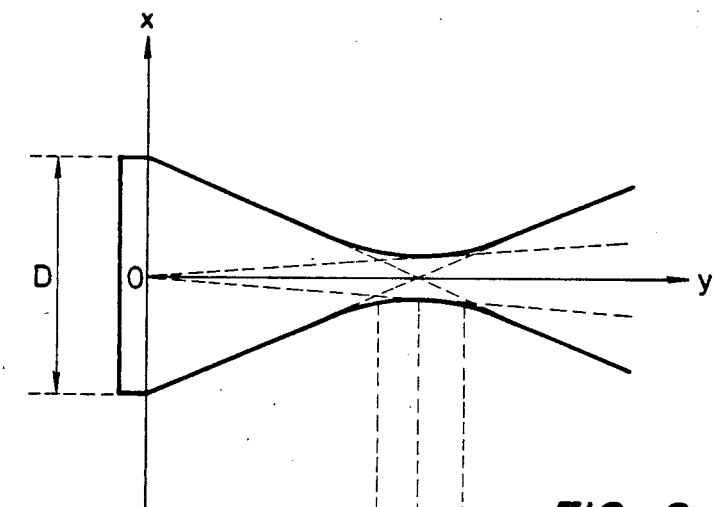
FIG. 1 is a schematic view of an ultrasonic beam.

FIG. 1 schematically illustrates the shape of a typical ultrasonic beam. In a transmission system, a physical beam is formed in practice whereas it is not formed in a reception system, but a space response function can be considered by substituting it by an equivalent beam. In the drawing, symbol D represents a diameter used for transmission or reception, x represents coordinates in the direction of diameter and y represents coordinates in the direction of depth.

Figure 2:
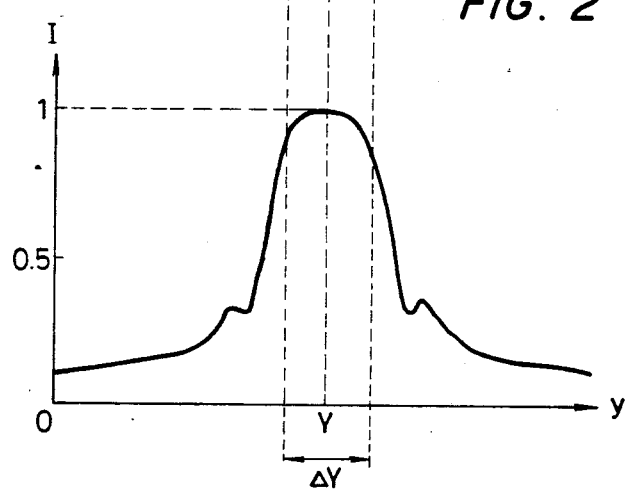
FIG. 2 is a diagram showing the change of the acoustic pressure on the center axis corresponding to the beam.

FIG. 2 illustrates the change of the acoustic pressure I on the center axis of the ultrasonic beam shown in FIG. 1 as a function of the depth y. The depth of focus $\Delta Y$ in the drawing can be expressed by the following equation $$\Delta Y = 2\lambda Y^2/D^2 \quad (1)$$

where Y is a focal length and $\lambda$ is the wave length of a ultrasonic wave.

To realize an easy operation, the depth of focus $\Delta Y$ is great in the conventional ultrasonic diagnosis system to form a focus system having a fixed focus or a plurality of mutually spaced-apart focal points. However, this system is not convenient for measuring the acoustic velocity. In the ultrasonic diagnosis system in accordance with the present invention, on the other hand, the depth of focus $\Delta Y$ must be made small in order to improve the measuring accuracy of the acoustic velocity.

Next, the principle of the measurement of the acoustic velocity in the present invention will be explained in detail.

Figure 3:
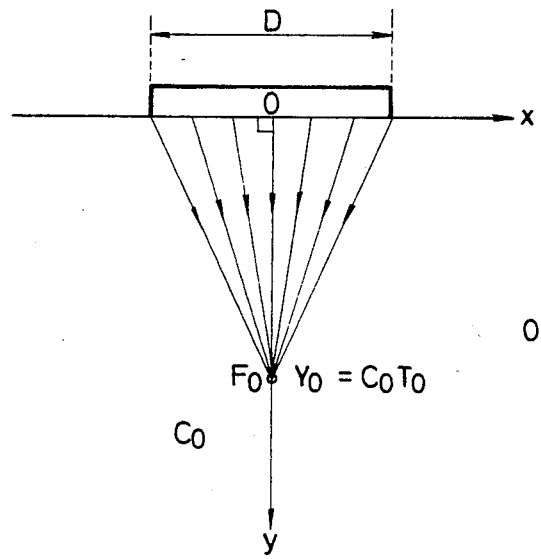
FIG. 3 is a schematic view useful for explaining the delay time for focus.

The following equation is established if the acoustic velocity to be assumed during imaging is $C_o$ and the focal length to be set, $Y_o$:

$$Y_o = C_o T_o \quad (2)$$

where $T_o$ is the half of the time required for a reflection signal to come back. A pulse-like ultrasonic wave is transmitted and received by setting a delay time $\tau(x)$ to be applied to the signal on the diameter to the following formula (see FIG. 3):

$$\tau(x) = \tau_o - (\sqrt{x^2 + Y_o^2} - Y_o)/C_o \qquad (3)$$
$$\approx \tau_o - x^2/(2C_oY_o)$$

where $\tau_o$ is a constant which is added so that the formula $\tau(x) \geqq 0$ is satisfied for all of x. When transmission and reception is effected in this manner, the following relation exists between the actual acoustic velocity C inside the body of the subject and the actual focal length Y with 2T (for x=0) representing the time required for the pulse to actually go and come back from the position of the reflector at which the highest intensity of the reflection signal is obtained:

$$Y = CT \qquad (4)$$

$$\tau(x) \approx \tau_o - x^2/(2CY) \qquad (5)$$

From equation (3) and (5), therefore, $$Y = C_oY_o/C \qquad (6)$$

From equation (2) and (4), $$C = \sqrt{\frac{C_oY_o}{T}} \qquad (7)$$

As expressed by equation (7), it is possible in principle to obtain the actual acoustic velocity C from the acoustic velocity $C_o$ which is assumed, the set focal length $Y_o$ and the time T required for the strong reflection signal to actually return.

When the accuracy of acoustic velocity measurement $\Delta C/C_o$ is estimated, the following formula is given:

$$\frac{\Delta C}{C_o} \approx \frac{\Delta T}{2T_o}$$
$$= \frac{\Delta Y}{2Y_o} = \frac{\lambda Y}{D^2}$$

When $\lambda = 0.3$ mm, Y=100 mm and D=60 mm, for example, the accuracy of 0.8% can be obtained.

The above is the fundamental principle of the present invention, but it is difficult to measure the acoustic velocity inside the body of the subject by use of the conventional transmission reception system having the fixed focus or a plurality of mutually spaced-apart focal points. For, the reflector having a sufficient reflecting intensity does not necessarily exist in the proximity of the focal position inside the body of the subject (the position whose distance from the body surface is Y given by equation (4)).

Figure 4:
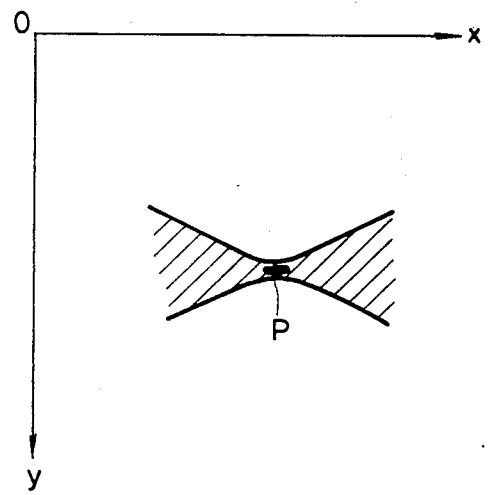
FIG. 4 is a schematic view of a space response function of a transmission-reception system.

As schematically shown in FIG. 4, the space response function of the transmission-reception system with respect to a point reflector takes the shape like a butterfly spreading the alae on both sides of the peak P and the difference appearing in the shapes of the reflection images is small between when the point reflector exists at the actual focal point and when it is deviated from the former. In this case, it seems more reliable to determine the deviation of setting of the acoustic velocity from the intensity rather than from the shape.

In the present invention, therefore, the set acoustic velocity $C_o$ is made variable and the formed ultrasonic image as well as the set acoustic velocity $C_o$ are displayed simultaneously. Accordingly, it becomes possible to observe the ultrasonic image of the reflector having a sufficient reflection intensity by making fine adjustment of the focal length Y inside the body of the subject given by equation (6) and to accurately measure the time required for the strong reflection signal to return. As can be understood from equation (6), fine adjustment of $C_o$ is equivalent to fine adjustment of $Y_o$ in order to make fine adjustment of Y, but the present specification will primarily deal with the former case for convenience' sake.

The operator of the system can measure the acoustic velocity in the following manner, for example. First, the assumed acoustic velocity $C_o$ and the focal length $Y_o$ are set and the formed image is then observed. Next, the operator pays special attention to a reflector which is not far from the focal point but has a sufficient reflection intensity and adjusts the acoustic velocity $C_o$ so that the image of the reflector is formed with the highest intensity. The mean acoustic velocity, which seems most reliable, from the body surface to the reflector can be obtained from $C_o$, $Y_o$ and T after completion of fine adjustment in accordance with equation (7).

To observe the image in the manner described above, it is not always easy to accurately determine the point where the image intensity becomes maximal. As shown in FIG. 2, the acoustic pressure on the center axis hardly changes within the depth of focus $\Delta Y$ described earlier so that the deviation of setting of the focal length or acoustic velocity can not be determined easily with a high level of accuracy. The depth of focus $\Delta Y$ is inversely proportional to the square of the diameter D of transmission and reception as expressed by equation (1). For this reason, it is possible in principle to increase the diameter D in order to improve the sensitivity to the deviation of the set acoustic velocity by reducing $\Delta Y$. For this purpose, however, the number of transducer elements must be increased, raising the cost of production of the system.

Figure 5:
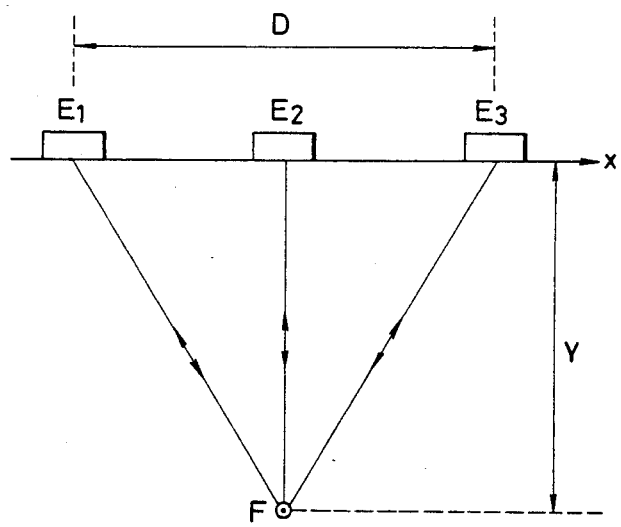
FIG. 5 is a diagram showing the construction of one embodiment of the present invention.
Figure 6:
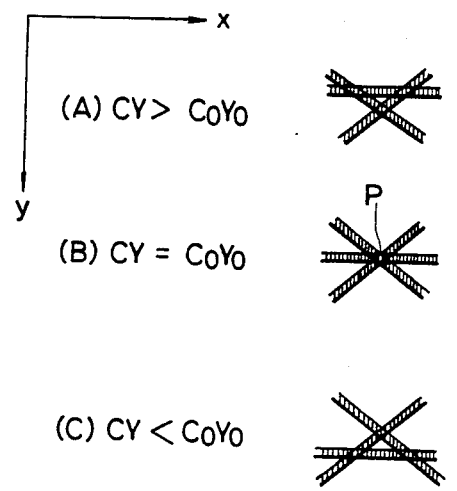
FIG. 6 is a diagram showing the space response function of the transmission-reception system to a dot reflector in the system shown in FIG. 5.

As the second proposal, therefore, the present invention proposes also a system having improved sensitivity to the deviation of the set acoustic velocity by adding the function of transmitting or receiving three ultrasonic waves from the mutually independent three directions to the focus F as shown in FIG. 5, in addition to the function described above. The space response function of the transmission reception system to the point reflector in accordance with this system assumes the shape in which three straight lines cross one another. The great advantage of this system is that the shapes of the points of intersection of these lines clearly change in accordance with the difference between the product $C_oY_o$ of the set acoustic velocity $C_o$ and the set focal length $Y_o$ and the product CY of the actual acoustic velocity C and the actual focal length Y, as depicted in FIGS. 6(A), (B) and (C). In this system, too, the diameter D must be increased as described above in order to improve the sensitivity to the deviation of the set acoustic velocity but another advantage is that the number of transducer elements to be used need not be increased.

Separately, the present invention proposes, as the third proposal, a system for effecting so-called "real time dynamic focus reception" by continuously scanning and receiving the focal length by one transmission instead of effecting fine adjustment of the focus in order to measure the time T required for the strong reflection signal to return. This system continuously scans and receives $Y_o$ in equation (3) so as to satisfy the following formula with t representing the passage of time from the time of transmission:

$$Y_o = C_o t/2 \qquad (8)$$

It can be understood that the actual focal length inside the body of the subject is scanned as expressed by the following equation, by putting equation (8) into (6):

$$Y = C_o^2/C \times t/2 \qquad (10)$$

In a real time dynamic focus reception system, the clearest image can be obtained when Y is scanned in such a manner as to satisfy the relation $Y = C \times t/2$. As can be seen from equation (10), therefore, the clearest image or the highest image intensity can be obtained when $C_o$ coincides with C.

The operator of the system can measure the acoustic velocity in the following manner, for example. First, the assumed acoustic velocity $C_o$ is set. Next, the operator pays specific attention to a reflector having a sufficient reflector intensity and adjusts the acoustic velocity $C_o$ so that the image of the reflector can be formed with the highest intensity. The $C_o$ value at the time of completion of adjustment represents the mean acoustic velocity itself, that seems most reliable, from the body surface to the reflector. In the case of this system, the operator can measure the acoustic velocity without the necessity of taking $Y_o$ and T into consideration, in particular. This is the characterizing feature of this system.

Hereinafter, the ultrasonic diagnosis system of the second and third proposals described earlier will be explained definitely with some embodiments thereof.

Figure 7:
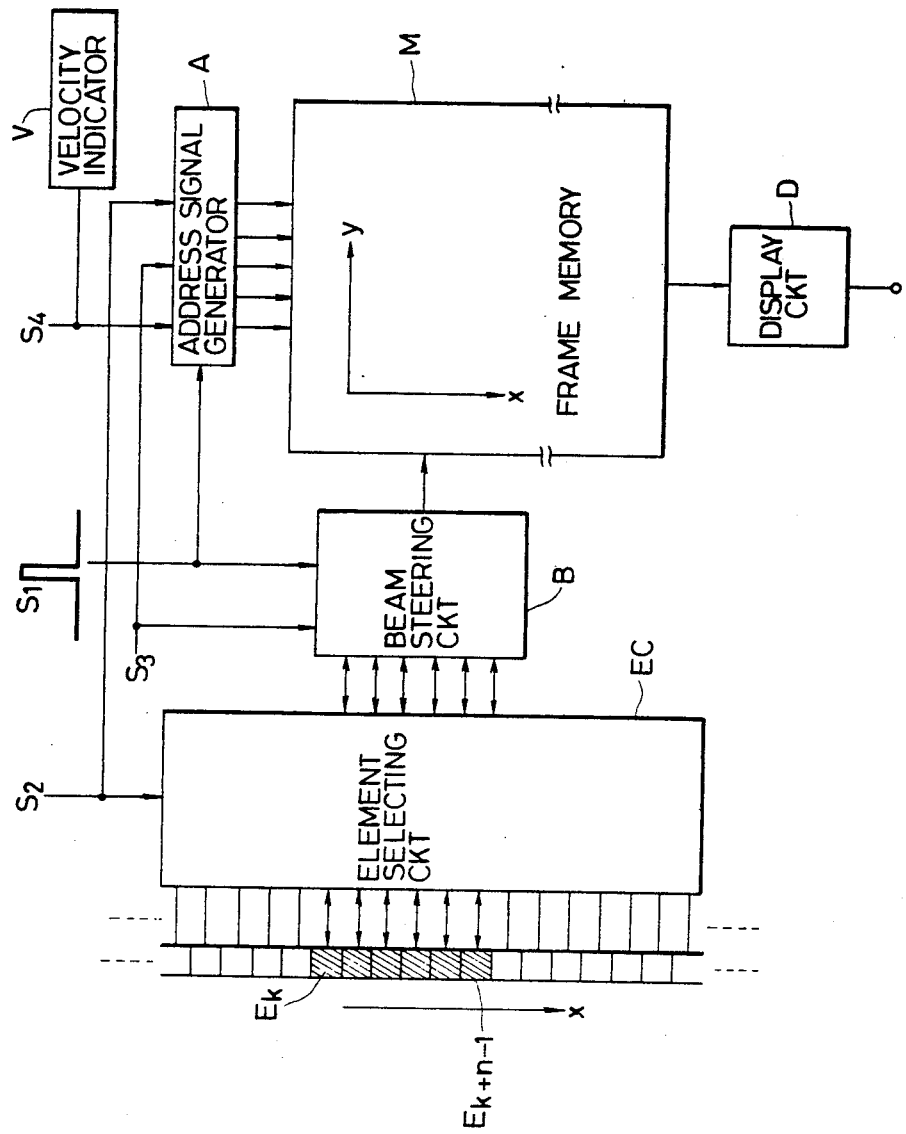
FIG. 7 is a block diagram showing another embodiment of the present invention.

FIG. 7 is a block circuit diagram of the system corresponding to the second proposal. In the drawing, symbols $E_1 \sim E_N$ represents transducer elements forming a transducer array $E_K \sim E_{K+n-1}$ are the elements selected by an element selecting circuit; B is a beam steering circuit for transmission and reception; M is a frame memory; A is an address signal generation circuit for the frame memory M; D is a display circuit; and V is a velocity indicator.

In the circuit construction described above, an echo signal obtained by transmitting and receiving the ultrasonic waves from three mutually independent directions is added on the frame memory, and $S_1$ through $S_4$ are signals which will be described later.

Figure 8:
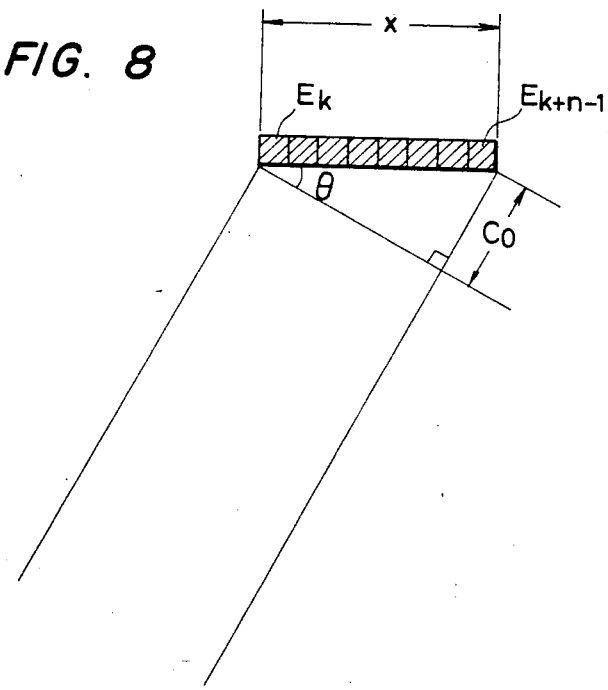
FIG. 8 is an operation diagram of the circuit shown in FIG. 7.

The beam steering circuit B for transmission and reception sends a transmission signal to the element selecting circuit EC in accordance with a transmission timing pulse $S_1$ and the address signal generation circuit A resets the y coordinates of the address. The element selecting circuit EC scans the selection element in accordance with a luster change-over signal $S_2$ and the address signal generation circuit A scans the x coordinates of the address. Furthermore, the beam steering circuit B for transmission and reception changes over the steering direction of the transmission and reception in accordance with a steering change-over signal $S_3$ and the address signal generation circuit A changes over the address scanning direction. The reception signal sent from the beam steering circuit for transmission and reception to the frame memory M is written while containing phase data. Whenever scanning for one frame is completed, the data on the frame memory M are sent to the display circuit D and are simultaneously reset. The address signal generation circuit A changes, in only a limited quantity, the address scanning direction in accordance with an assumed acoustic velocity signal $S_4$. In other words, as shown in FIG. 8, the address scanning angle $\theta$ is controlled in accordance with the assumed acoustic velocity $C_o$ so as to satisfy the relation:

$$\sin \theta = C_o \tau / x \qquad (11)$$

where x is the diameter used simultaneously and $\tau$ is the delay time difference between both ends of the diameter.

In the system of this embodiment, there is no specific focal length and a reflection echo signal assumes the state shown in FIG. 6(B) for the reflectors at all the distances when the acoustic velocity is in agreement with $C_o$. Accordingly, the operator observes the image while adjusting the assumed acoustic velocity $C_o$ and when the image of the reflector which is to be specifically observed reaches the state shown in FIG. 6(B), he may obtain the approximate value of C, which seems most reliable, from $C_o$ displayed by the velocity indicator V at that time.

Figure 9:
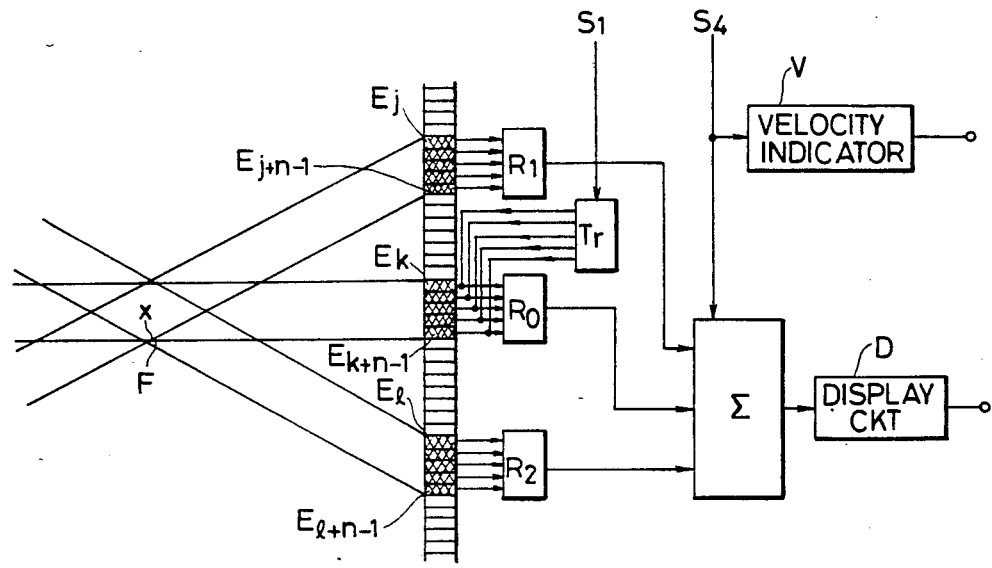
FIG. 9 is a diagram showing the construction of another embodiment of the present invention.

FIG. 9 is a block circuit diagram showing another embodiment of the present invention, which transmits a pulse-like ultrasonic wave signal by one transducer block and receives the signal by three transducer blocks formed by separating the reflection echo signal.

The transducer block composed of elements $E_K \sim E_{K+n-1}$ transmists the pulse-like ultrasonic wave signal and the three transducer blocks $E_j \sim E_{j+n-1}$, $E_k \sim E_{k+n-1}$ and $E_l \sim E_{l+n-1}$ respectively receive the signal. $S_1$ is the transmission pulse signal described above, $T_r$ is a transmission circuit and $R_o$, $R_1$ and $R_2$ are reception circuits. F represents the focus of reception, and $\Sigma$ is a summation circuit for focusing which can minutely change the delay time in accordance with the assumed acoustic velocity.

In comparison with the system of the foregoing embodiment shown in FIG. 7, the system of this embodiment has the advantage that an error due to the movement of the subject does not occur because the signals in the three directions necessary for imaging are simultaneously received.

Incidentally, in the embodiment shown in FIG. 7, the relation between transmission and reception may be reversed and in such a case, only one set of reception circuits is used in place of the simultaneous use of three sets of the reception circuits so that the cost of the transmission circuit becomes sometimes more economical than the reception circuit.

FIGS. 10 and 11 are block circuit diagrams of the systems in accordance with the third embodiment described already. In the systems of these embodiments, the diameter of reception is set to at least two times the diameter of transmission and imaging is carried out while a large number of focal points are changed over for one transmission thereby realizing a so-called "real time dynamic focus reception method".

Figure 10A:
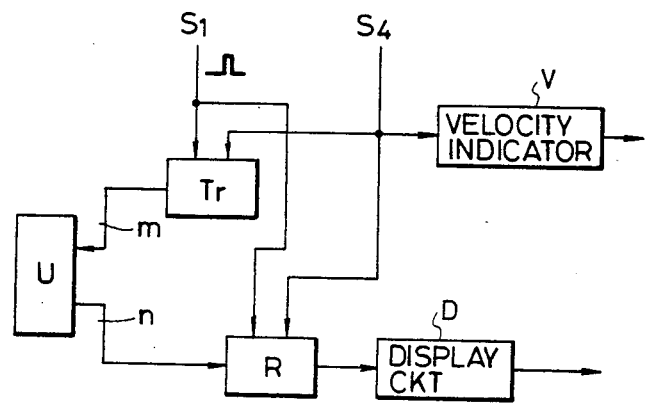
FIGS. 10a and 10b are a diagram showing construction of another embodiment and curves of acoustic velocity, respectively.

In the circuit of the embodiment shown in FIG. 10(a), the transmission timing pulse $S_1$ is applied to the transmission circuit $T_r$ and to the reception circuit R. The transmission circuit $T_r$ generates a transmission wave signal in synchronism with the transmission timing pulse $S_1$ in accordance with the value of the assumed acoustic velocity signal $S_4$ and sends it to an ultrasonic transducer array U. The reception circuit R effects dynamic focus reception while changing the focal length $Y_o$ in response to the time passed T from the transmission timing pulse $S_1$ in accordance with the value of the assumed acoustic velocity signal $S_4$ and sends the resulting image signal to the image display circuit D. The assumed acoustic velocity signal is also sent to the velocity indicator V.

Figure 10B:
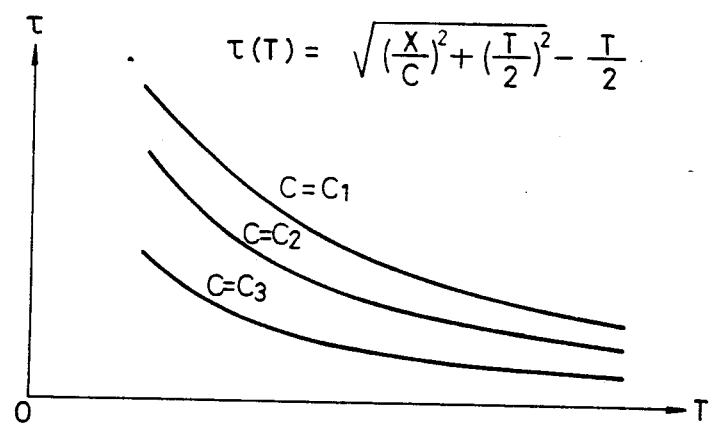

FIG. 10(b) shows the delay time $\tau$ given to the signal from one element in the reception diameter. To realize dynamic focusing, $\tau$ is changed with T in accordance with the function shown in the drawing, but the function itself changes as shown in the drawing with the assumed acoustic velocity C being the parameter. Here, symbol x represents the distance between the element to be observed and the center of diameter.

Figure 11A:
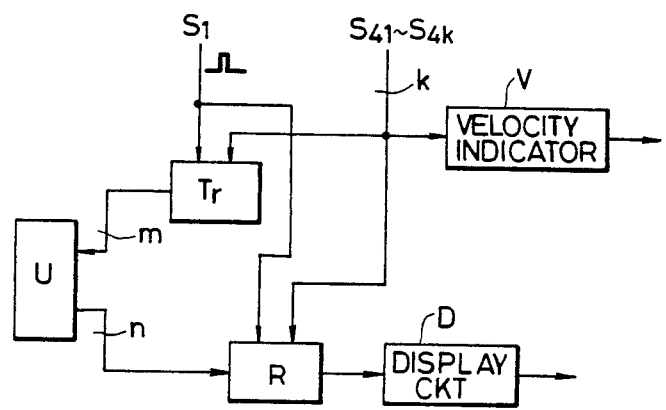
FIGS. 11a and 11b are a diagram showing construction of a further embodiment and a curve showing a step-wise change in acoustic velocity, respectively.

The embodiment shown in FIG. 11(a) makes it possible to set the assumed acoustic velocity in the number k, i.e., from $S_{41}$ to $S_{4k}$. It is known that the acoustic velocity inside the body of the subject is not constant but varies by several percents from portion to portion. Accordingly, in the system of this embodiment, K different acoustic velocities are assumed in the direction of depth to enable imaging. The reception circuit R is constructed in such a fashion that dynamic focus reception is effected while changing the assumed acoustic velocity in K different manners in accordance with the passage of time from the transmission timing pulse.

Figure 11B:
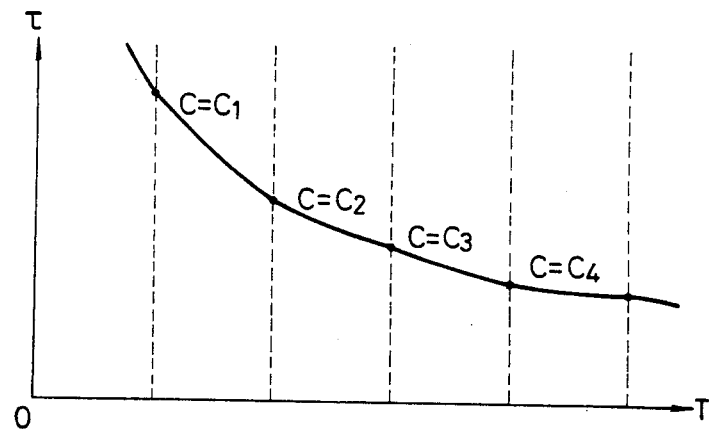

FIG. 11(b) shows the relation between the delay time $\tau$ and T in this case. The assumed acoustic velocity is changed step-wise in accordance with the passage of time T.

Figure 12:
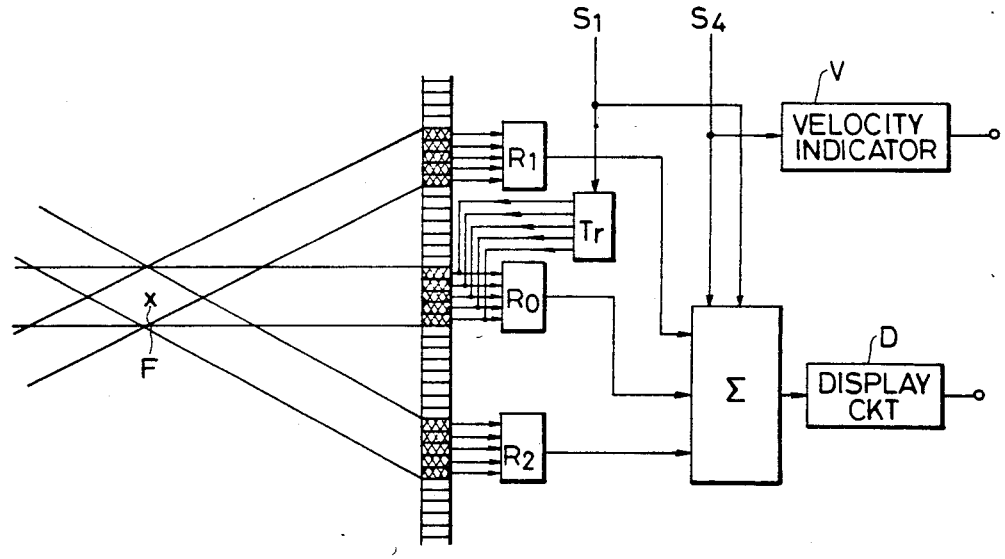
FIG. 12 is a diagram showing the construction of another embodiment.

FIG. 12 is a circuit diagram showing still another embodiment of the present invention. In the circuit of the embodiment shown in FIG. 9, this embodiment furnishes the summation circuit for focusing with the function of the real time dynamic focus described above so as to take a photograph while changing the delay time in summation in accordance with the passage of time from the transmission timing pulse $S_1$ and with the assumed acoustic velocity $S_4$. Needless to say, this arrangement makes it possible to form an image of the entire region expanding in the direction of depth in which a transmitted wave travels per transmission.

In the same way as in the system shown in FIG. 7, the system of this embodiment does not have any specific focal length and the reflection echo signal attains the state shown in FIG. 6(B) for the reflector at all the distances when the acoustic velocity becomes $C_o$ in this embodiment, too.

Figure 13:
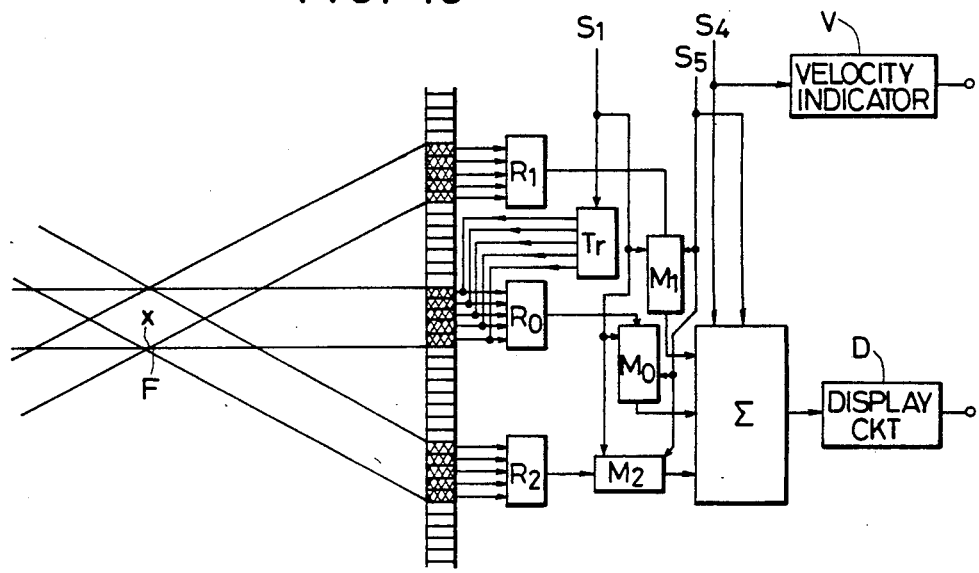
FIG. 13 is a diagram showing the construction of another embodiment.

FIG. 13 shows still another embodiment of the present invention. The difference of this embodiment from the embodiment shown in FIG. 12 is that it has memories $M_o$, $M_1$ and $M_2$ that start writing by the transmission timing pulse $S_1$ and reading by a signal $S_5$ which is applied to the summation circuit for focusing $\Sigma$ in place of the transmission timing pulse $S_1$. This embodiment has the advantage that since the reception signals are once stored in the memories $M_o$, $M_1$, $M_2$, the assumed acoustic velocity signal $S_4$ for the same reception signal can be changed to display the image. This arrangement provides the effect that the determination of the acoustic velocity, which seems most reliable, becomes easier.

Figure 14:
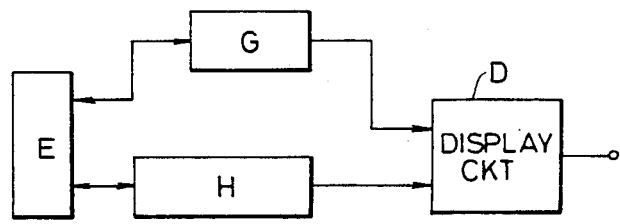
FIG. 14 is a diagram illustrating operation of the present invention.

FIG. 14 shows an application example of the present invention. The signal transmitted and received by transducer system E is exchanged between the conventional ultrasonic imaging system G and the ultrasonic image system H in accordance with the present invention. The output signals of both imaging systems G, H are transmitted to the image display circuit D and the two images are displayed either alternately or simultaneously. Since the image by the ultrasonic imaging system H is principally based upon the measurement of acoustic velocity, a system which is easier to operate can be realized because it covers the problem that a side lobe level or the like becomes greater than that of the image formed by the conventional ultrasonic imaging system G.

Next, another embodiment of the present invention will be explained. The principle of this new embodiment will be described with reference to FIGS. 15 and 16 prior to the description of the embodiment.

Figure 15:
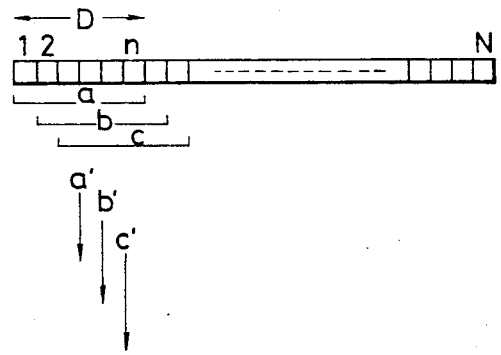
FIG. 15 shows a conventional linear type ultrasonic diagnosis system.

FIG. 15 shows a conventional linear type ultrasonic diagnosis system. Symbols 1 through N represent all the elements arranged of probes and 1 through n represent the elements arranged inside the transmission-reception diameter D. When the position of the transmission-reception diameter is sequentially moved to a, b and c, the ultrasonic beam is also moved to a', b' and c'. In the conventional system, the transmission-reception diameter is substantially the same and a relatively small diameter is employed in view of cost performance.

Figure 16:
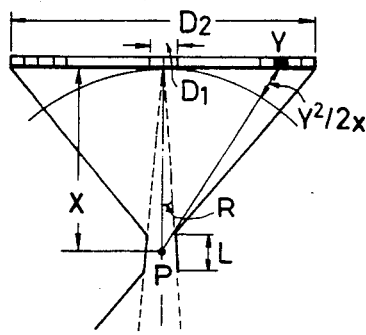
FIG. 16 shows the principle of an embodiment of the present invention.

FIG. 16 shows the principle of the embodiment of the present invention, in which the transmission diameter $D_1$ is different from the reception diameter $D_2$ and this reception diameter $D_2$ is greater than that of the conventional system. Accordingly, the direction characteristics of the transmission wave are substantially determined by the reception diameter $D_2$, and the resolution R as well as the depth of focus L are given by the following equation, respectively:

$$R = \lambda/D_2 \qquad (11)$$

$$L = 4\lambda(x/D_2)^2 \qquad (12)$$

where $\lambda$ is the wavelength and x is the depth. When depth x=100 mm, wavelength $\lambda$=0.43 mm and the reception diameter $D_2$=64 mm, for example, the resolution R=0.007 (rad)=0.4 (deg.) and the depth of focus L=4 mm.

When the resolution becomes high and the depth of focus becomes small as described above, the influence of the acoustic velocity in a medium becomes greater. In other words, high resolution can not be obtained if the set acoustic velocity when designing the system is greately deviated from the acoustic velocity in the medium of the subject.

As shown in FIG. 16, the following relation can be established:

$$V_o \cdot \tau_o(Y) = \sqrt{x^2 + y^2} - x \qquad (13)$$

where x is the depth, Y is the element arranged (with the origin being positioned at the center of the diameter) and $\tau_o(Y)$ and $V_o$ are the initial values of the delay time for convergence and the acoustic velocity inside the medium, respectively. Here, the right side is the value which is solely determined by the geometric shape. It will be assumed that V is the accurate acoustic velocity inside the medium and the delay time $\tau_o(Y)$ is changed to the delay time $\tau(Y)$ so that the image of the reflector having the depth x is focused. In this case, the following relation should be established:

$$V \cdot \tau(Y) = \sqrt{x^2 + y^2} - x \qquad (14)$$

From equation (13) and (14), the accurate acoustic velocity V of the medium is given by:

$$V = V_o \cdot \tau_o(Y)/\tau(Y) \qquad (15)$$

Since $V_o$ and $\tau_o(Y)$ are known in advance, the acoustic velocity V can be measured by determining $\tau(Y)$.

Figure 17:
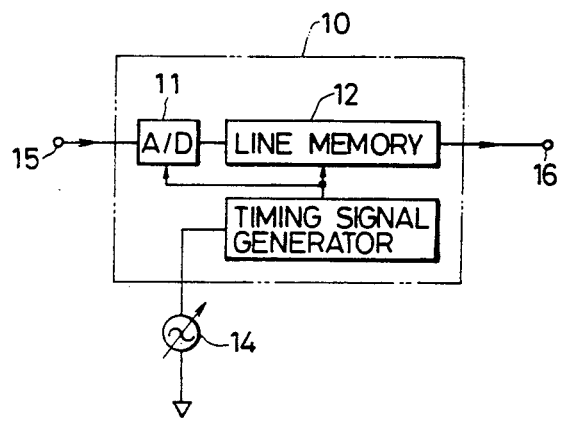
FIG. 17 shows an embodiment of a one-channel reception wave delay circuit.

FIG. 17 shows an embodiment of a one-channel reception wave delay circuit. Reference numeral 10 represents a delay circuit; 11 is an A-D convertor; 12 is a line memory; 13 is a timing signal generator; and 14 is a clock generator. Reference numeral 15 represents an input terminal and 16 represents an output terminal. When the clock frequency of the clock generator 14 is $f_o$, the delay time $\tau(Y)$ when the clock frequency is changed to $f_{op}$ is given by the following equation with $\tau_o(Y)$ representing the delay time of the delay circuit 10:

$$\tau(Y) = \tau_o Y \cdot \frac{f_o}{f_{op}} \qquad (16)$$

From equation (15) and (16), therefore, $$V = V_o \cdot \frac{f_o}{f_{op}} \qquad (17)$$

In this manner, the accurate acoustic velocity inside the medium can be measured from the change of the clock frequency $f_{op}/f_o$ of the variable delay means and the initial acoustic velocity $V_o$. At the same time, depth x is also determined accurately.

It is theoretically possible to use the observation of the operator to determine whether or not the reflector P is focused but this method involves the problem that it depends upon the subjectivity of the operator to some extent. Hence, the following embodiment is equipped with automatic focus means for automatically adjusting the focus upon a predetermined reflector.

FIG. 18 shows the function of the automatic focus of this embodiment. FIG. 18a is a schematic view of the point reflector displayed on a display 17 of the ultrasonic imaging system and its position is $(x_o, y_o)$. However, $x_o$ does not always represent the actual distance to the point reflector and is a value obtained by halving the product of the assumed acoustic velocity $V_o$ and the passage of time from the transmission. Here, x represents the direction of depth and y represents the lateral direction. This embodiment includes a y direction cursor 18 for positioning the point reflector to be focused in the display image in the y direction and an x direction cursor 19 for positioning it in the x direction and determining the initial value $f_o$ of the clock frequency corresponding to the depth.

Figure 18A:
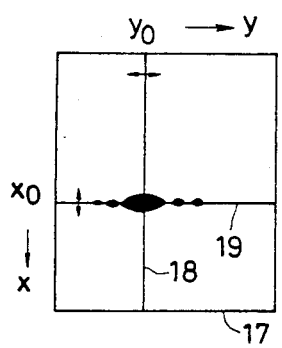
FIGS. 18a–18d show waveforms for explaining operation of another embodiment.
Figure 18B:
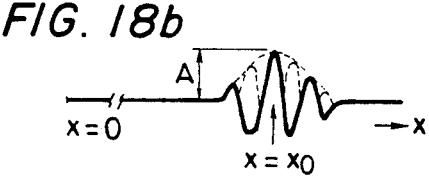

In FIG. 18b, an A mode waveform at $y = y_o$ is represented by solid line and a detected waveform, by dotted line.

The peak value of this detected waveform is assumed to be A.

Figure 18C:
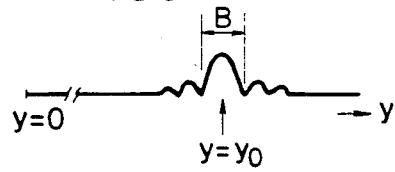

FIG. 18c shows a Z signal of the display at $x = x_o$. This is a direction beam pattern of the system and the beam width at the first zero point is assumed to be B.

Figure 18D:
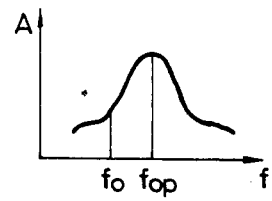

FIG. 18d shows the relation between the frequency f of the clock generator 14 shown in FIG. 17 and the detected waveform A in FIG. 18b. In this drawing, the peak value A becomes maximal at $f_{op}$ which is different from the intial value $f_o$ of the clock frequency and a point target image is focused.

Similarly, it is obvious that the clock frequency f may be made variable so that the direction resolution B becomes minimal.

Figure 19:
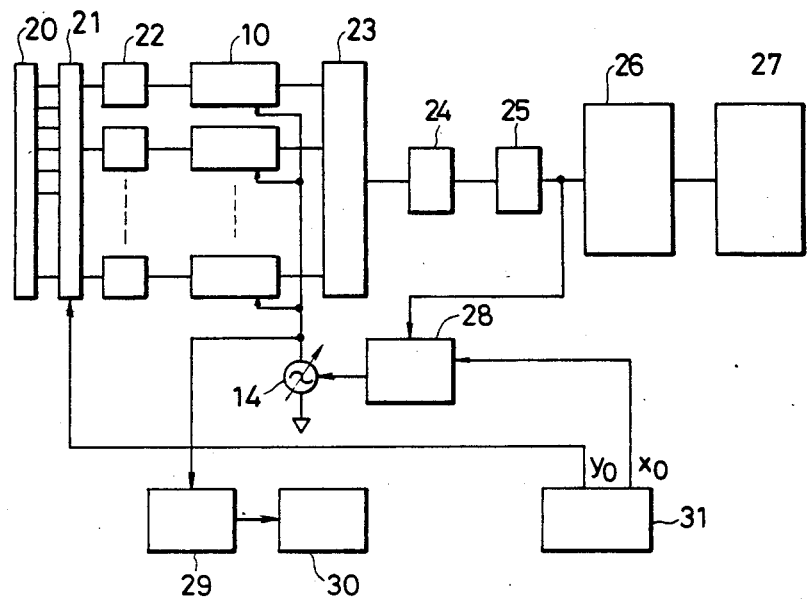
FIG. 19 shows another embodiment.

FIG. 19 shows a definite example of the automatic focus function explained with reference to FIG. 18. Reference numeral 20 represents a transducer array; 21 is a selector for selecting the transmission-reception diameter from all of the transducer elements 22 is a pre-amplifier; 23 is an adder; 24 is a compression circuit; 25 is a detection circuit; 26 is an image memory; 27 is an image display; and 28 is an automatic focus detection circuit which detects the focal point by so-called "mountain climbing" techniques, for example. Reference numeral 29 represents a calculation circuit which calculates the acoustic velocity from the change of the clock frequency in accordance with equation (7) and reference numeral 31 represents an operation panel which positions the cursors 18, 19 shown in FIG. 18a to the position of the point target on the image and produces a position signal $x_o$, $y_o$ at that time.

In accordance with the construction described above, the carcel position $y_o$ is applied to the selector 21 to select the transmission-reception diameter. The reception signal is subjected to phase matching through the pre-amplifier 22, the delay means 10 and the adder 23 and the detected waveform shown in FIG. 18b is obtained through the compression circuit 24 and the detection circuit 25. This detected waveform is applied to the automatic focus detection circuit 28.

A signal in the proximity of the depth $x = x_o$ is cut out from the detected waveform for one line in the scanning direction $y = y_o$ in the automatic focus circuit 28, and the clock frequency f of the clock signal generator 14 is gradually increased from the initial value $f_o$ as shown in FIG. 18d so as to automatically detect the clock frequency $f_{op}$ at which the peak value A of the detected waveform becomes maximal.

When $f_{op}$ is determined in the manner described above, the calculation circuit 29 executes the calculation of equation (17) to display the acoustic velocity V on the velocity indicator 30.

In the foregoing description, the explanation of the operation of the image memory 26 is omitted. When the beam width of the beam pattern shown in FIG. 18c is used as a parameter, however, it is necessary to change the clock frequency using one line data of the image memory 26 at the depth $x = x_o$ so that the beam width B becomes minimal.

In the embodiments described above, the mean acoustic velocity between the oscillator and the reflector is measured.

When a living body is to be dealt with, however, the medium acoustic velocity is generally non-uniform so that there arises the necessity of measuring the acoustic velocity at each portion of the living body.

As a model of a medium having a non-uniform acoustic velocity, the present invention will be therefore be explained about the case in which the model has a layered structure in the direction of depth, with reference to FIG. 20.

It will be now assumed that the reflectors $P_1$, $P_2$ have the depth $x_1$, $x_2$, respectively, the portions between the oscillator and the reflector $P_1$ and between the reflector $P_1$ and the reflector $P_2$ consist of homogeneous media, which are called I and II layers, respectively.

The acoustic velocity $V_1$ of the I layer is determined in accordance with the method of the present invention described already, and the position $x_1$ of the reflector $P_1$ is then determined in accordance with the following equation using the return time $T_1$ of the reflection wave at this time:

$$x_1 = T_1 V_1/2 \quad (18)$$

Next, the position $x_2$ is likewise determined between the reflector $P_2$ and the oscillator in accordance with the following equation:

$$x_2 = T_2 \hat{V}/2 \quad (19)$$

where $\hat{V}$ is the mean acoustic velocity between the I and II layers. The propagation time $T_3$ for going and returning inside the II layer is given by:

$$T_3 = T_2 - T_1 \quad (20)$$

Accordingly, the acoustic velocity $V_2$ to be measured is given by:

$$V_2 = \frac{2(x_2 - x_1)}{T_3} \quad (21)$$

Figure 20A:
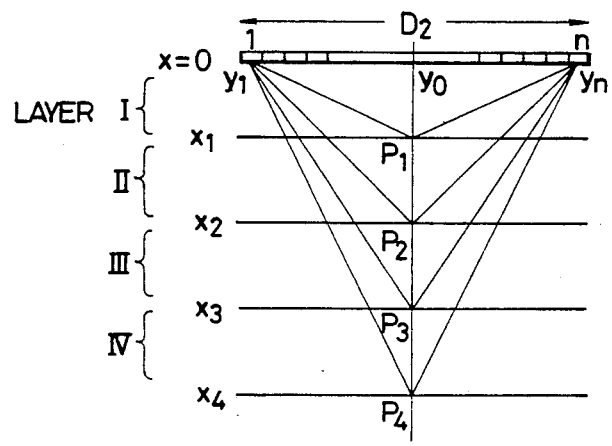
FIGS. 20a–20c show diagrams for explaining operation of another embodiment.
Figure 20B:
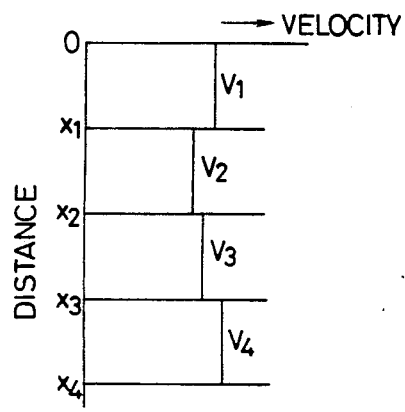

When the subject has a multi-layered structure consisting of I, II, III and IV layers such as shown in FIG. 20a, this embodiment makes it possible to sequentially determine the acoustic velocities $V_1$, $V_2$, $V_3$, $V_4$ from the near distance side as shown in FIG. 20b.

Figure 20C:
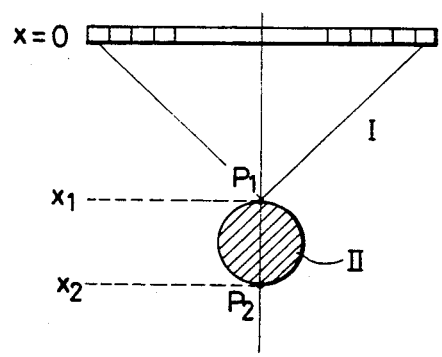

Even when a spherical heterogeneous substance such as a medium (II) exists in the homogeneous medium (I) such as shown in FIG. 20c, this method makes it possible to measure the acoustic velocity inside the heterogeneous medium by setting the reflectors $P_1$ and $P_2$ as shown in the drawing.

In FIG. 20a, the acoustic velocity is assumed to be uniform inside each of layers I through IV of the heterogeneous medium but in the case of a living body, it sometimes occurs that the acoustic velocity is not uniform inside each layer in the x direction.

Figure 21:
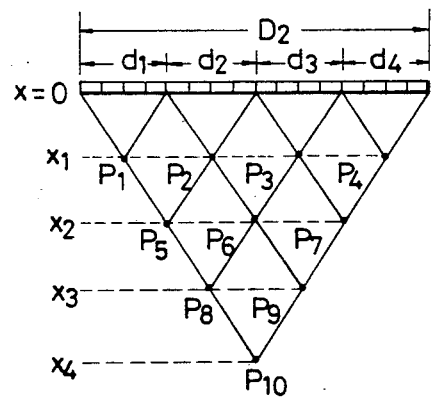
FIG. 21 shows a further embodiment.

FIG. 21 shows an embodiment of the present invention to measure the acoustic velocity at each portion. Symbols $d_1$ through $d_4$ are partial diameters and $p_1$ through $p_{10}$ are reflectors. Mutually independent variable delay means are connected to the partial diameters $d_1$ through $d_4$, respectively.

First, the acoustic velocity between the depth $x=0$ and $x=x_1$ is measured for the reflectors $p_1$ through $p_4$ at the depth $x_1$ using the partial diameters $d_1$ through $d_4$. Next, the acoustic velocity between the depth $x=x$ and $x=x_2$ is measured for the reflectors $p_5$ through $p_7$ at the depth $x_2$ using the partial diameters $d_1+d_2$, $d_2+d_3$ and $d_3+d_4$, respectively. In the same way as described above, the acoustic velocity is sequentially measured for each of the reflectors $p_8$ through $p_{10}$.

In this manner, the acoustic velocity at each portion can be sequentially measured for a medium which is heterogeneous not only in the direction of depth but also in the lateral direction.

As described above, the present invention can automatically measure the mean acoustic velocity in a medium in accordance with the reflection method.

The present invention can also measure sequentially the acoustic velocity at each portion from a near distance side even when a medium is heterogeneous in the direction of depth or in the lateral direction. The acoustic velocity distribution inside a body can also be measured.

The acoustic velocity data of the tissues of a living body thus obtained are useful for tissue characterization and greatly contributes to the medical science.

What is claimed is:

1. An ultrasonic diagnosis system comprising:
   a transducer array having a plurality of transducer elements;
   transmitting means for driving said transducer elements so that a pulse-like ultrasonic wave is transmitted from said transducer array to an object;
   receiving means for receiving reflection signals from said transducer elements, the reflection signals being indicative of reception at said transducer elements of waves reflected from said object;
   signal generating means for generating an adjustable signal representative of an assumed acoustic velocity for said object;
   indicating means for indicating the assumed velcoity of said object;
   focusing means for delaying respective reflection signals in accordance with a delay amount distribution and for summing the delayed reflection signals, the delay amount distribution being determined in accordance with the assumed acoustic velocity so that a receiving ultrasonic beam of said transducer elements is focused to a predetermined focal point; and
   display means for displaying an image of said object by converting an output of said focusing means to a visual signal;
   whereby an actual acoustic velocity of said object is indicated by said indicating means when said adjustable signal of said signal generating means is adjusted so that an image of a reflector on said image of said object displayed by said display means has the highest intensity.

2. An ultrasonic diagnosis system according to claim 1, further comprising selecting means for selecting one number of transducer elements of said transducer array in response to said tansmitting means and another number of transducer elements of said transducer array in response to said receiving means, a greater number of transducer elements of said transducer array being selected in response to said receiving means than the number of transducer elements of said transducer array in response to said transmitting means so that the receiving aperture of said transducer array is larger than the transmitting aperture of said transducer array.

3. An ultrasonic diagnosis system according to claim 2, wherein said selecting means is responsive to said receiving means for selecting three groups of transducer elements of said transducer array, the three groups of transducer elements being located at the center and both ends of said transducer array.

4. An ultrasonic diagnosis system according to claim 1 further comprising selecting means for selecting transducer elements of said transducer array, said selecting means being responsive to said receiving means for selecting three groups of transducer elements of said transducer array, said three groups of transducer elements being located at the center and both ends of said transducer array.

5. An ultrasonic diagnosis system according to claim 1, wherein said focusing means provides for scanning said predetermined focal point along a line of a depth direction for achieving real time dynamic focusing.

6. An ultrasonic diagnosis system comprising:

a transducer array having a plurality of transducer elements;

transmitting means for repeatedly driving said transducer elements so that pulse-like ultrasonic waves are repeatedly transmitted from said transducer array to an object;

receiving means for receiving reflection signals representative of perception at said transducer elements of said transducer array of reflection waves from reflectors in said object;

delay means for delaying respective reflection signals in accordance with a changeable delay distribution;

summing means for summing the delayed reflection signals;

self-running control means for providing a gradually changing control signal for controlling said changeable delay amount distribution to said delay means;

automatic focus detection means for stopping the gradual change of the gradually changing control signal when a peak value of the output of said summing means becomes a maximum value; and calculating means for calculating the acoustic velocity of said object in accordance with an initial value and the stopped value of the gradually changing control signal.

7. A method for measuring acoustic velocity of an object comprising the steps of:

transmitting a pulse-like ultrasonic wave from a transducer array having a plurality of transducer elements to the object by applying driving signals to the transducer elements;

receiving from the transducer elements reflection signals indicative of reception at the transducer elements of reflecting waves from reflectors in the object by summing the reflection signals from the transducer elements;

delaying at least one of respective driving signals applied to the transducer elements and respective reflection signals from the transducer elements in accordance with a predetermined delay amount distribution so that at least one of the pulse-like ultrasonic wave and a receiving ultrasonic beam are focused to a point at a predetermined distance;

determining the delay amount distribution in accordance with the predetermined distance and an assumed acoustic velocity;

measuring the time elapsed for the pulse-like ultrasonic wave to be transmitted and a reflection signal of the highest intensity to return to the transducer array; and determining an actual acoustic velocity of the object in accordance with the predetermined distance, the assumed acoustic velocity and the elapsed time.

8. A method for measuring acoustic velocity of an object comprising the steps of:

transmitting a pulse-like ultrasonic wave from a transducer array having a plurality of transducer elements to the object by applying driving signals to the transducer elements;

receiving from the transducer elements reflection signals indicative of reception at the transducer elements of reflecting waves from reflectors in the object by summing the reflection signals from the transducer elements delaying at least one of respective driving signals applied to the transducer elements and respective reflection signals from the transducer elements in accordance with a predetermined delay amount distribution so that at least one of the pulse-like ultrasonic wave and a receiving ultrasonic beam are focused to a point at a predetermined distance;

determining the delay amount distribution in accordance with the predetermined distance and an assumed acoustic velocity;

displaying an image of the reflection signals; and determining the acoustic velocity of the object by adjusting the assumed acoustic velocity and repeating the steps of transmitting, receiving and displaying so as to obtain an image of a reflector having the highest intensity, the acoustic velocity of the object corresponding to the assumed acoustic velocity utilized for obtaining the image having the highest intensity.

9. A method for measuring acoustic velocity of an object comprising the steps of:

transmitting a pulse-like ultrasonic wave from a transducer array having a plurality of transducer elements to the object by applying driving signals to the transducer elements;

receiving from the transducer elements reflection signals indicative of reception at the transducer elements of reflecting waves from reflectors in the object by summing the reflection signals from the transducer elements;

delaying respective reflection signals from the transducer elements in accordance with a time varying delay amount distribution so that a focus point of a receiving ultrasonic beam is scanned along a line of depth direction;

determining the time varying delay amount distribution in accordance with an assumed acoustic veleocity;

displaying an image of a reflection signal; and determining the acoustic velocity of the object by adjusting the assumed acoustic velocity and repeating the steps of transmitting, receiving and displaying so as to obtain an image having the highest intensity, the acoustic velocity of the object corresponding to the assumed acoustic velocity for obtaining the image having the highest intensity.

* * * * *